United States Patent [19]

Bocharov et al.

[11] 4,115,469
[45] Sep. 19, 1978

[54] METHOD OF DIMERIZATION OF OLEFINS

[76] Inventors: Jury Nikolaevich Bocharov, ulitsa Dokukina 3, korpus 1, kv. 13; Andrei Alexandrovich Antonov, Profsojuznaya ulitsa 87, korpus 3, kv. 85; Viktor Alexandrovich Kabanov, Lomonosovsky prospekt 14, kv. 108; Marina Alexandrovna Martynova, ulitsa Stasovoi 4, kv. 34; Stanislav Konstantinovich Pluzhnov, pereulok Yazykovsky 5, kv. 104; Vladimir Ivanovich Smetanjuk, ulitsa Stasovoi 4, kv. 34, all of Moscow, U.S.S.R.

[21] Appl. No.: 779,262

[22] Filed: Mar. 18, 1977

[51] Int. Cl.$^2$ .................................................. C07C 3/10
[52] U.S. Cl. ........................ 260/683.15 D; 252/429 B
[58] Field of Search ............................. 260/683.15 D; 252/429 B

[56] References Cited

U.S. PATENT DOCUMENTS

| | | | |
|---|---|---|---|
| 3,737,474 | 6/1973 | Dunn | 260/683.15 D |
| 3,872,026 | 3/1975 | Dunn | 252/429 B |

*Primary Examiner*—C. Davis
*Attorney, Agent, or Firm*—Lackenbach, Lilling & Siegel

[57] ABSTRACT

The method of dimerization of olefins having from 2 to 4 carbon atoms consists in that at least one said olefin is mixed, in a medium of hydrocarbon or halogenated hydrocarbon solvents at a temperature of from 0° to 100° C and a pressure from 1 to 40 atmospheres, with a catalyst, which is a graft copolymer of a natural or a synthetic carbon-chain rubber with vinylpyridine; said copolymer swells in said solvents and contains from 0.5 to 40 per cent of fragments of polyvinylpyridine that are complexed with a nickel salt, and contains also from 2 to 50 mole per cent of -AlRX- units, where R is an alkyl having not more than 8 carbon atoms, and X is a halogen, the aluminum atom being bound with the main chain of the copolymer through the carbon atom. The atom ratio of Al/Ni is from 1 to 20.

Said catalyst is characterized by high stability and preserves it initial activity for a long period of time. It is not crushed in the process and is easy to recover. The catalyst is characterized also by high selectivity: the butene-1 content of a mixture of butenes, obtained by dimerization of ethylene, is 92 to 96 per cent. The methyl-pentene content of the dimerizate, obtained by dimerization of propylene, is 90 to 95 per cent.

3 Claims, No Drawings

METHOD OF DIMERIZATION OF OLEFINS

BACKGROUND OF THE INVENTION

The invention relates to petrochemistry, and more particularly it relates to methods of dimerization of olefins. Olefins obtained by the herein-proposed method can be used as monomers and comonomers in the manufacture of polyolefins, as intermediates in the manufacture of monomers for synthesizing rubber, etc.

Known in the art are methods for dimerization of olefins by mixing them with various catalysts of the homogeneous or heterogeneous type.

Homogeneous catalysts consisting of an organoaluminum compound and a compound of a transition metal with low-molecular ligands, containing the elements standing in the V or IV groups of the Periodic Table (nitrogen, oxygen, phosphorus, sulphur) have certain disadvantages. The main drawback is the difficulty of isolation of the target products in their pure state, since special methods are required to separate the components that are present in one phase, and also the difficulty of performing the continuous process. As a rule, all methods are batch processes. Moreover, homogeneous catalysts are relatively unstable in time and cannot be recovered.

Dimerization of olefins with heterogeneous catalysts can be both batch and continuous processes. But as the reaction mixture is stirred in the process, or otherwise handled, heterogeneous catalysts become crushed and much of it is lost.

Furthermore, known homogeneous and heterogeneous catalysts fail to give high yields of butene-1 by dimerizing ethylene. (cis- and trans-butene-2, having a concentration of 85 to 98 per cent, are mainly produced). It is not possible to obtain high yields of methylpentenes in dimerization of propylene either (the methylpentene content of the dimerizate is 69 per cent maximum).

Known at the present time is the method of dimerization of olefins, having not over 12 carbon atoms, consisting in mixing at least one of said olefins with a two-component catalyst, consisting of an organoaluminum compound, having the general formula $R_nAlX_{3-n}$, where R is an alkyl having not more than 12 carbon atoms, X is a halogen, and $n$ is 1 or 2; and a copolymer of vinylpyridine with a polyvinyl-substituted aromatic compound (e.g. divinylbenzene, trivinylbenzene), said copolymer containing 75 to 90 per cent by weight of polyvinylpyridine fragments that complexed with a nickel salt of an organic or a mineral acid; the molar ratio of the organoaluminum compound to the nickel salt is 1 – 100. Said olefins and said two-component catalyst are mixed in a medium of hydrocarbon or halocarbon solvents at a temperature of $-50°$ to $+150°$ C and a pressure of 1 to 100 atmospheres.

The catalyst used in this method (which is insoluble in the reaction medium) is characterized by the same disadvantages that are inherent in the known heterogeneous catalysts.

SUMMARY OF THE INVENTION

One object of this invention is to provide a method of dimerization of olefins, having from 2 to 4 carbon atoms, that gives high yields of butene-1 and methylpentene.

Another object of the invention is to provide a method of dimerization of olefins, having from 2 to 4 carbon atoms, utilizing a catalyst possessing high stability that can easily be recovered.

Still another object of the invention is to provide a method of dimerization of olefins that could be easily realized on both continuous and batch principles.

In accordance with these and other objects, the invention consists in that, in a medium of hydrocarbon or halocarbon solvents, at a temperature of from 0° to 100° C, preferably at 20° to 70° C, and a pressure from 1 to 40 atmospheres, preferably under a pressure from 1 to 10 atmospheres, at least one said olefin is mixed with a catalyst, which swells in said solvents, and which is a grafted copolymer of natural or synthetic carbon-chain rubber with vinylpyridine, said copolymer containing from 0.5 to 40 per cent by weight of polyvinylpyridine fragments that are complexed with a salt of nickel of an organic or a mineral acid, and containing also from 2 to 50 mole per cent of -AlRX-units, where R is an alkyl having not more than 8 carbon atoms, and X is a halogen, the aluminum atom being connected with the main chain of the copolymer through a carbon atom; the atomic ratio Al/Ni is from 1 to 20, preferably from 3 to 6.

The catalyst is characterized by high selectivity: the dimerization process yields 92 to 96 per cent of butene-1 in the resultant mixture of butenes; dimerization of propylene gives mainly methylpentenes (the methylpentene content of the obtained dimerizate is 90 to 95 per cent).

In contrast to the known heterogeneous catalysts, the proposed catalyst is in the gel form. It is not crushed, can be easily recovered, and reused many times without loss of its initial activity.

The proposed method of dimerizaton of olefins having from 2 to 4 carbon atoms is realized by mixing at least one said olefin with a catalyst in a medium of hydrocarbon solvents (aliphatic, aromatic hydrocarbons), or halogenated hydrocarbon solvents, at a temperature from 0° to 100° C, preferably from 20° to 70° C, and a pressure from 1 to 40 atm, preferably from 1 to 10 atm., in batch reactors (with stirring), or in passthrough tube reactors of continuous action. Individual olefins, and such as ethylene, propylene, butene, or mixtures thereof, e.g. a mixture of ethylene and propylene, or a mixture of ethylene with butene, can be dimerized by the proposed method.

As has been said, the catalyst that should be used according to the proposed invention, is a graft copolymer of natural, or synthetic carbon-chain rubber with vinylpyridine, that swells in said solvents. The copolymer contains from 0.5 to 40 per cent by weight of polyvinylpyridine fragments that are complexed with a nickel salt of an organic or a mineral acid, and also from 2 to 50 mole per cent of -Al RX-units, where R is an aryl having not more than 8 carbon atoms, preferably from 2 to 4 carbon atoms, and X is a halogen, preferably chlorine, the aluminum atom being connected with the main copolymer chain through the carbon atom; the atom ratio of Al/Ni is from 1 to 20, preferably from 3 to 6.

Either natural or synthetic carbon-chain rubber can be used in the manufacture of the catalyst. These can be, e.g., 1.2-polybutadiene, cis- and trans-polybutadiene, isoprene rubber, ternary copolymers of ethylene, propylene, and non-conjugated diene.

Rubber (60 to 99.5 per cent by weight) undergoes a radical grafted copolymerization with 0.5 – 40 per cent by weight of vinylpyridine, e.g. 4-vinylpyridine, 2- vinylpyridine, 3-vinylpyridine, 2-methyl-5-vinylpyridine, in a medium of hydrocarbon or halogenated hydrocarbon solvents at a temperature from 40° to 70° C. Azobisisobutyronitrile can be used as the initiator of the radical copolymerization. After copolymerization, the copolymer is cross-linked by peroxidic initiators, e.g. benzoyl peroxide.

The obtained copolymer is then reacted with a salt of nickel, e.g. nickel chloride, nickel bromide, nickel oleate, nickel acetylacetonate, in a medium of said solvents, at a temperature from 10° to 50° C. The resulting graft copolymer that swells in said solvents, contains from 0.5 to 40 per cent by weight of polyvinylpyridine fragments that are complexed with a nickel salt. The obtained nickel-containing copolymer is washed thoroughly with a solvent to remove possible traces of unreacted nickel salt.

The obtained nickel-containing copolymer is acted upon with a dialkylaluminum hydride, preferably with diisobutylaluminum hydride, in a medium of an absolute hydrocarbon solvent, at a temperature from 0° to 100° C, or with a trialkylaluminum, preferably with triisobutylaluminum, at a temperature of from 100° to 160° C. The quantity of dialkylaluminum hydride or trialkylaluminum is from 2 to 50 mole per cent with respect to the unit of the rubber chain. The obtained product, in a medium of said solvents, is acted upon by the stoichiometric quantity (with respect to the aluminum content of rubber) of chlorine, or aluminum halide, preferably aluminum chloride, or alkylaluminum dihalide, preferably ethylaluminum dichloride, or isobutylaluminum dichloride, or with an at least ten-fold excess (with respect to stoichiometric quantity) of a dialkylaluminum halide, preferably diisobutylaluminum chloride, at a temperature of from 20° to 50° C.

The obtained gel-like catalyst is washed thoroughly with a solvent to remove possible traces of unreacted low molecular organometallic compounds.

The catalyst used according to the proposed method is made in the form of granules that swell in said solvents to the particle size of 0.1 to 5 mm. These granules are readily permeable for the reagents and the formed reaction products throughout their entire volume.

DESCRIPTION OF THE PREFERRED EMBODIMENT

For a better understanding of the invention, the following examples of its practical embodiment are given by way of illustration.

EXAMPLE 1

An 75-ml ampoule is loaded with 1 g of 1,2-polybutadiene, 0.11 g of 4-vinylpyridine, and 40 ml of heptane. Upon dissolution of rubber, the solution is degassed, and 0.04 g of azobisisobutyronitrile in 5 ml of benzene is added. The ampoule is kept at a temperature of 70° C for 10 hours. Now 0.04 g of benzoyl peroxide in 5 ml of benzene is added to the ampoule contents and the ampoule is again kept at a temperature of 80° C for another ten hours. The obtained graft copolymer of rubber with 4-vinylpyridine is separated by filtration, washed two times with small portions (10 ml) of benzene, and dried in vacuum. Said copolymer swells in hydrocarbon and halocarbon solvents. The poly-4-vinylpyridine content of the copolymer is about 13 per cent by weight.

The obtained graft-copolymer, having particles sizing 2 to 3 mm, is loaded in the quantity of 1 g into a 75-ml glass reactor provided with a stirrer. 0.24 g of nickel acetylacetonate and 30 ml of heptane are added, the reaction mixture is stirred at a temperature of 20° C for 20 hours. The polymer granules are then washed several (4 to 6) times with 10-ml portions of heptane to remove unreacted nickel acetylacetonate and dried in vacuum. The resultant graft copolymer contains fragments of poly-4-vinylpyridine that are complexed with the molecules of nickel acetylacetonate (nickel-containing copolymer). The nickel content of the copolymer is 1.3 per cent by weight.

10 ml of a 0.5 M solution of diisobutylaluminum hydride in absolute heptane, and 20 ml of absolute heptane per se, are added to the obtained nickelic copolymer in vacuum. The obtained mixture is kept for three hours at a temperature of 60° C, and then for another three hours at a temperature of 100° C. Further 10 ml of a 0.5 M solution of ethylaluminum dichloride in absolute heptane are added to the reactor contents and the mixture is kept for ten hours at a temperature of 20° C. The granules of the catalyst, containing 10 mole per cent of -Al-(iso-Bu)Cl-units, are washed thoroughly with absolute heptane to remove low-molecular organoaluminum compounds, and dried in vacuum. The atom ratio of Al/Ni in the catalyst is 6. The swelling power of the catalyst granules is as follows: 0.1 g of the granules takes in 0.7 ml of heptane at a temperature of 20° C.

The obtained catalyst is loaded, in the quantity of 0.2 g, into a 50-ml glass reactor provided with a stirrer, and 15 ml of absolute heptane are added. The mixture is stirred for 30 minutes at a temperature of 40° C, and then ethylene is passed into the reactor at a temperature of 40° C and a pressure of 2 atmospheres. The reaction is continued for two hours. The products of dimerization are distilled into a receiver. The yield is 3 g of butenes containing 92 per cent of butene-1.

EXAMPLE 2

A flask, having the capacity of 75 ml and provided with a stirrer, is loaded with 1 g of granulated graft copolymer of 1,2-polybutadiene with 4 -vinylpyridine, containing 9 per cent by weight of fragments of poly-4-vinylpyridine (the copolymer is obtained by a procedure similar to that described in Example 1), 0.13 g of nickel chloride and 30 ml of heptane. The reaction mixture is stirred for 20 hours at a temperature of 20° C. The polymer granules are then washed several times with heptane to remove unreacted nickel chloride, and dried in vacuum. The nickel content of the copolymer is 1.2 per cent by weight.

Then 10 ml of a 0.5 M solution of diisobutylaluminum hydride in absolute heptane, and 30 ml of absolute heptane per se are added to the obtained nickel-containing copolymer in vacuum. The mixture is kept for three hours at a temperature of 60° C and then for another three hours at a temperature of 100° C. 10 ml of a 0.5 M solution of ethylaluminum dichloride in absolute heptane are added into the reactor, and the mixture is kept for ten hours at a temperature of 20° C. The granules of the catalyst containing about 20 mole per cent of —Al-(iso—Bu)—Cl— units, are then washed thoroughly with absolute heptane to remove unreacted low-molecular organoaluminum compounds, and dried in vacuum. The atom ratio of Al/Ni in the catalyst is about 10. 0.1 g of the granules soak 0.4 ml of heptane at a temperature of 20° C.

A tubular reactor is loaded with the obtained catalyst and 20 ml of absolute decane are added. Ethylene is then passed. The dimerization process is carried out at a temperature of 20° C and a pressure of 3 atmospheres. The dimerizate is collected in a receiver. Samples are taken at certain intervals of time and the obtained butenes are analysed by gas-liquid chromatography. The results are given in the Table.

Table

| Time, in minutes | Butene-1 content of dimerizate, in per cent |
|---|---|
| 10 | 96.0 |
| 30 | 95.0 |
| 60 | 95.1 |
| 120 | 94.9 |

EXAMPLE 3

An ampoule having a capacity of 75 ml, provided with a stirrer is loaded with 0.6 g of granulated cross-linked grafted copolymer obtained by radical copolymerization of 1,2-polybutadiene with a ternary copolymer of ethylene, propylene and ethylidene norbornene and with 4-vinylpyridine (the procedure of copolymerization is the same as described in Example 1; the weight ratio of said reagents 1 : 4 : 1 respectively). Now 0.15 g of nickel oleate and 30 ml of heptane are added to the reactor, the reaction mixture is stirred for 10 hours at a temperature of 20° C, and the polymer granules are washed several times with heptane to remove unreacted nickel oleate with subsequent drying in vacuum. The obtained copolymer contains about 1.45 per cent by weight of nickel.

5.3 ml of a 0.5 M solution of diethylaluminum hydride in absolute heptane, and 20 ml of absolute heptane per se, are added to the obtained nickel-containing copolymer and the reaction mixture is kept for 5 hours at a temperature of 50° C. Then 5.3 ml of a 0.5 M solution of ethylaluminum dibromide in absolute heptane are added and the mixture is kept at a temperature of 20° C for ten hours. The granules of the catalyst, containing 7 mole per cent of —Al(ethyl)Br— units are washed thoroughly with absolute heptane to remove low-molecular organoaluminum compounds and dried in vacuum. The atom ratio of Al/Ni is about 3. 0.1 g of the granules soaks 0.55 ml of heptane at a temperature of 20° C.

A 50-ml reactor provided with a stirrer is loaded with 0.3 g of the obtained granulated catalyst and 20 ml of absolute heptane. Then ethylene is passed into the reactor at a temperature of 20° C and a pressure of 1 atm. In 1 hour, the formed butenes are removed from the reactor. The rate of ethylene dimerization is 1.5 kg of butenes per gram of Ni per hour. The butene-1 content of the obtained butene mixture is 95 per cent.

The temperature in the reactor is then raised to 40° C and ethylene is dimerized at a pressure of 1 atm. The formed butenes are removed from the reactor in 90 minutes. The rate of ethylene dimerization is 1.1 kg of butenes per gram of Ni per hour. The butene-1 content of the obtained butene mixture is 94 per cent.

The temperature is further raised to 60° C and ethylene is dimerized under a pressure of 2 atmospheres. The reaction products are removed from the reactor in 1 hour. The rate of ethylene dimerization is 0.7 kg of butenes per gram of Ni per hour. The butene-1 content of the butene mixture is 96 per cent.

EXAMPLE 4

A reactor containing 0.3 g of the catalyst used in Example 3 (after the removal of the products of ethylene dimerization and the solvent) is loaded with 20 ml of absolute heptane. Then propylene is passed into the reactor, and dimerization is carried out at a temperature of 40° C and a pressure of 1.5 atm. The solvent and the reaction product are removed from the reactor in 1 hour. The rate of dimerization of propylene is 0.8 kg of hexenes per gram of Ni per hour. The methylpentene content of the obtained hexane mixture is about 95 per cent.

Then 20 ml of absolute chlorobenzene are added to the reactor and propylene is dimerized at a temperature of 0° C and a pressure of 1 atm. The reaction products and the solvent are removed from the reactor in 1 hour. The rate of propylene dimerization is 0.9 kg of hexenes per gram of Ni per hour. The methylpentene content of the obtained hexene mixture is 92 per cent.

EXAMPLE 5

A reactor is loaded with 0.3 g of the catalyst similar to that used in Example 3 (the atom ratio Al/Ni is 1), and 20 ml of absolute toluene. The ethylene is passed into the reactor and dimerized at a temperature of 40° C and a pressure pf 1 atm. The dimerization products are removed from the reactor in 1 hour. The rate of ethylene dimerization is 1.1 kg of butenes per gram of Ni per hour. The butene-1 content of the obtained butene mixture is 94 per cent.

The temperature in the reactor is then raised to 100° C and the ethylene is dimerized under a pressure of 10 atm for an hour. The rate of dimerization of ethylene is 0.3 kg of butene per gram of Ni per hour. The butene-1 content of the obtained butene mixture is 95 per cent.

EXAMPLE 6

A reactor provided with a stirrer is loaded with 0.3 g of granulated cross-linked graft-copolymer obtained by radical copolymerization of 1,2-polybutadiene with a ternary copolymer of ethylene, propylene, and ethylidene norbornene (the weight ratio of the reagents is 2:1) and with 4-vinylpyridine (the content of fragments of poly-4-vinylpyridine in the cross-linked grafted copolymer is 40 per cent by weight). Now 0.12 g of nickel bromide and 30 ml of heptane are added to the reactor. The reaction mixture is stirred for 10 hours at a temperature of 20° C. The polymer granules are washed several times with heptane to remove unreacted nickel bromide, and dried in vacuum.

The obtained nickel-containing copolymer is reacted with dioctylaluminum hydride, and then with ethylaluminum dichloride in conditions specified in Example 1. The granules of the obtained catalyst, containing 50 mole per cent of —Al(octyl)Cl— units, are washed thoroughly with absolute heptane to remove low-molecular organoaluminum compounds and dried in vacuum. The atom ratio of Al/Ni is 12.

A reactor containing the obtained catalyst is loaded with 20 ml of butene-1 and ethylene is passed into it. The mixture of butene-1 with ethylene is dimerized at a temperature of 0° C and a pressure of 2 atmospheres. In one hour the reaction products are distilled off and analyzed. The yield of hexenes, consisting of 50 per cent of methylpentenes and 50 per cent of linear hexenes, is 0.3 g.

EXAMPLE 7

A reactor provided with a stirrer is loaded with 1 g of cross-linked graft-copolymer obtained by radical copolymerization of natural rubber with 1,2-polybutadiene and 2-vinylpyridine (the copolymerization conditions are the same as in Example 1; the weight ratio of natural rubber to 1,2-polybutadiene is 9:1; the content of fragments of poly-2-vinylpyridine in the cross-linked graft-copolymer is 0.5 per cent by weight). Now 0.05 g of nickel acetylacetonate and 25 ml of heptane are added and said copolymer is reacted with nickel acetylacetonate in conditions specified in Example 1. The obtained nickel-containing copolymer is reacted in conditions specified in Example 1 with 2 ml of 0.5 M solution of diisobutylaluminum hydride in absolute heptane, and then with 2 ml of 0.5 M solution of ethylaluminum dichloride in absolute heptane. The granules of the catalyst containing 2 mole per cent of —Al(iso-butyl)-Cl— units, are washed thoroughly with absolute heptane to remove low-molecular compounds, and dried in vacuum. The atom ratio of Al/Ni is about 20. 0.1 g of the granules soaks 0.8 ml of heptane at a temperature of 20° C.

Then the ethylene is dimerized at a temperature of 70° C and a pressure of 40 atmospheres in a medium of absolute heptane. The reaction is discontinued in two hours and butenes (0.8 g) containing about 95 per cent of butene-1, are collected in a receiver.

EXAMPLE 8

A pass-through reactor provided with a stirrer and connected to a circulating compressor, is loaded with 0.5 g of the granulated catalyst similar to that used in Example 3 (the atom ratio of Al/Ni is 5), and 40 ml of absolute decane. The ethylene is passed and dimerized at a temperature of 30° C. and a pressure of 2 atmospheres. The ethylene is circulated in the system at a rate of 20 to 50 g per hour. The products of dimerization are withdrawn from the reactor with a stream of the circulating ethylene and collected in the trap. The process is continued for 100 hours. The productivity of the catalyst is 120 kg/g Ni. The obtained mixture of butenes (consisting of butene-1 cis-, and transbutene-2) contains about 94 per cent of butene-1.

What is claimed is:

1. A method of dimerization of olefins having from 2 to 4 carbon atoms, consisting in that at least one of said olefins is mixed with a gel-like catalyst in a medium of solvents selected from the group consisting of hydrocarbon and halocarbon solvents, at a temperature of from 0° to 100° C and a pressure of from 1 to 40 atmospheres, said catalyst being a graft-copolymer of rubber, selected from the group consisting of natural and synthetic carbon-chain rubber, with vinylpyridine, said copolymer swelling in said solvents, and containing from 0.5 to 40 per cent by weight of fragments of polyvinylpyridine that are complexed with a salt of nickel, and also contains from 2 to 50 mole per cent of —AlRX- units, where R is an alkyl having not more than 8 carbon atoms, and X is a halogen, the aluminum atom being connected with the main chain of the copolymer through the carbon atom; the atom ratio of Al/Ni is from 1 to 20.

2. A method according to claim 1, in which olefins are mixed with the catalyst at a temperature from 20° to 70° C and a pressure of from 1 to 10 atmospheres.

3. A method according to claim 1, in which use is made of a catalyst which is a graft-copolymer of synthetic carbo-chain rubber with 4-vinylpyridine, that swells in said solvents and contains from 0.5 to 40 per cent by weight of fragments of poly-4-vinyl-pyridine, that are complexed with a nickel salt, and contains also from 2 to 50 mole per cent of —AlRx- units, where R is an alkyl having from 2 to 4 carbon atoms, and X is chlorine, the aluminum atom being bound with the main chain of the copolymer through the carbon atom; the atom ratio of Al/Ni is from 3 to 6.

* * * * *